United States Patent [19]

Granzow, Jr. et al.

[11] 4,167,663

[45] Sep. 11, 1979

[54] BLOOD WARMING APPARATUS

[75] Inventors: Daniel B. Granzow, Jr., Arlington Heights; Robert J. Froehlich, Mt. Prospect, both of Ill.

[73] Assignee: Baxter Travenol Laboratories, Inc., Deerfield, Ill.

[21] Appl. No.: 761,926

[22] Filed: Jan. 24, 1977

[51] Int. Cl.$^2$ .............................................. H05B 1/02
[52] U.S. Cl. ............................ 219/497; 128/214 A; 219/502; 219/494; 219/330; 219/309
[58] Field of Search ............... 219/502, 308, 309, 328, 219/330, 331, 299, 497, 491, 499, 216, 294, 494; 128/214 A, 214 B; 333/22 F, 22 R

[56] References Cited

U.S. PATENT DOCUMENTS

| 3,484,651 | 12/1969 | Riley | 219/497 |
|---|---|---|---|
| 3,590,215 | 6/1971 | Anderson | 219/308 |
| 3,614,385 | 10/1971 | Horstmann | 128/214 A |
| 3,742,188 | 6/1973 | Sundbye | 219/330 X |
| 3,821,516 | 6/1974 | Hayes et al. | 219/497 |
| 3,903,395 | 9/1975 | Hamstra | 219/497 |
| 3,903,883 | 9/1975 | Pecina et al. | 219/308 |
| 3,925,139 | 12/1975 | Simmons | 219/497 |
| 3,946,200 | 3/1976 | Juodikis | 219/497 |

FOREIGN PATENT DOCUMENTS

2360124  6/1975  Fed. Rep. of Germany ........... 219/308

Primary Examiner—Roy N. Envall, Jr.
Assistant Examiner—M. Paschall
Attorney, Agent, or Firm—Henry W. Collins; Paul C. Flattery; George H. Gerstman

[57] ABSTRACT

An apparatus for warming blood and other parental fluids as they are infused through a disposable flow system includes a pair of heating elements which heat the blood as it passes through a warming bag provided in the flow system. The heating elements are recurringly switched on and off with a duty cycle dependent on both the temperature of the blood at the output of the warming bag, and the temperature differential between the output and input of the bag to maintain the blood at a predetermined temperature independent of flow rate. A duty cycle alarm circuit senses current supplied to the heating elements and trips the main circuit breaker of the apparatus to terminate operation in the event current is continuously applied over a predetermined interval of time, and temperature range and door alarm circuits sound an alarm if the output temperature of the blood falls outside of a predetermined range or if the operator attempts to remove the warming bag from the apparatus while the apparatus is in operation.

26 Claims, 14 Drawing Figures

BLOOD WARMING APPARATUS

BACKGROUND OF THE INVENTION

This invention is directed generally to fluid warming apparatus and, more particularly, to an apparatus for warming cold parental fluids such as whole blood for intervenous injection or transfusion procedures.

Whole blood is commonly stored in blood banks at a temperature of 4° C. until infused into a patient, at which time it is necessary that the blood be warmed to or slightly below the 37° C. temperature of the human body if hypothermia and the attendant risk of ventricular fibrillation and cardiac asystole are to be avoided. For applications where substantial and unpredictable quantities of blood are required, as where a patient hemorrages during surgery, it is preferable that blood in storage be transferred substantially directly into the patient, since this avoids warming blood which is not subsequently used.

The present invention provides an effective and efficient system for dry warming blood or other parental fluids to body temperature during the process of infusing such fluids into the patient. It is a feature of the invention that the temperature of the infused blood is maintained substantially constant at 37° C. substantially independent of flow rates, which may vary from 0 to 150 ml per minute depending on the needs of the patient. A further feature is that the operation of the apparatus, as well as the temperature of the blood leaving the apparatus, is continuously monitored, and in the event of a malfunction operation is terminated and an alarm is sounded. Novel self-test provisions within the apparatus allow the operator to verify the operation of these monitoring circuits prior to placing the blood warming apparatus in service.

Sterility of the blood is maintained and contamination of the apparatus is avoided by use of a disposable flow system having a blood warming bag which fits within the apparatus in thermal communication with electric heating elements. An additional feature of the invention provides an alarm in the event of inadvertent removal of the blood processing bag from the apparatus, and AC-coupled sensing circuitry which measures the temperature of the blood at the inlet and outlet portions of the blood processing bag automatically controls the operation of the heating elements to more accurately maintain the output temperature of the blood.

Accordingly, it is a general object of the present invention to provide a new and improved apparatus for warming blood and other parental fluids prior to infusion into the human body.

It is another object of the present invention to provide new and improved apparatus for maintaining blood and other parental fluids at a substantially constant temperature over a wide range of flow rates.

It is another object of the present invention to provide new and improved blood warming apparatus which provides improved protection against malfunction.

It is another object of the present invention to provide a new and improved blood warming apparatus which is convenient to operate and requires a minimal amount of operator supervision.

It is another object of the present invention to provide a new and improved blood warming apparatus which requires a minimal set-up time and may be conveniently set-up and operated in a variety of different environments.

SUMMARY OF THE INVENTION

The invention is generally directed to a fluid warming apparatus for heating a refrigerated fluid such as bood to a predetermined nominal temperature prior to infusion at flow rates variable over a substantial predetermined range. The apparatus includes housing means defining a heating chamber for the fluid within the apparatus, and at least one electric heater element operable from an applied electric current in thermal communication with the fluid in the heating chamber for heating the fluid as it passes through the apparatus. A control circuit responsive to the input and output temperature of the fluid within the compartment generates a heater control signal dependent on both the output temperature and the flow rate of the fluid, and switch means electrically connected between the heating element and a source of electrical current respond to the heater control signal by controlling the application of current to the heating element to maintain the fluid at the predetermined nominal temperature notwithstanding variations in the flow rate thereof.

The invention is more specifically directed to the above apparatus wherein the control circuit establishes a recurring on-off duty cycle for the heater element dependent on both the output temperature and temperature differential of the fluid in the apparatus, and wherein this mode of operation is obtained by means of a ramp generator providing a ramp function having a slope dependent on the difference between input and output temperatures, and a comparitor which provides an output based upon this ramp function reaching a voltage level dependent on the output temperature of the fluid.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
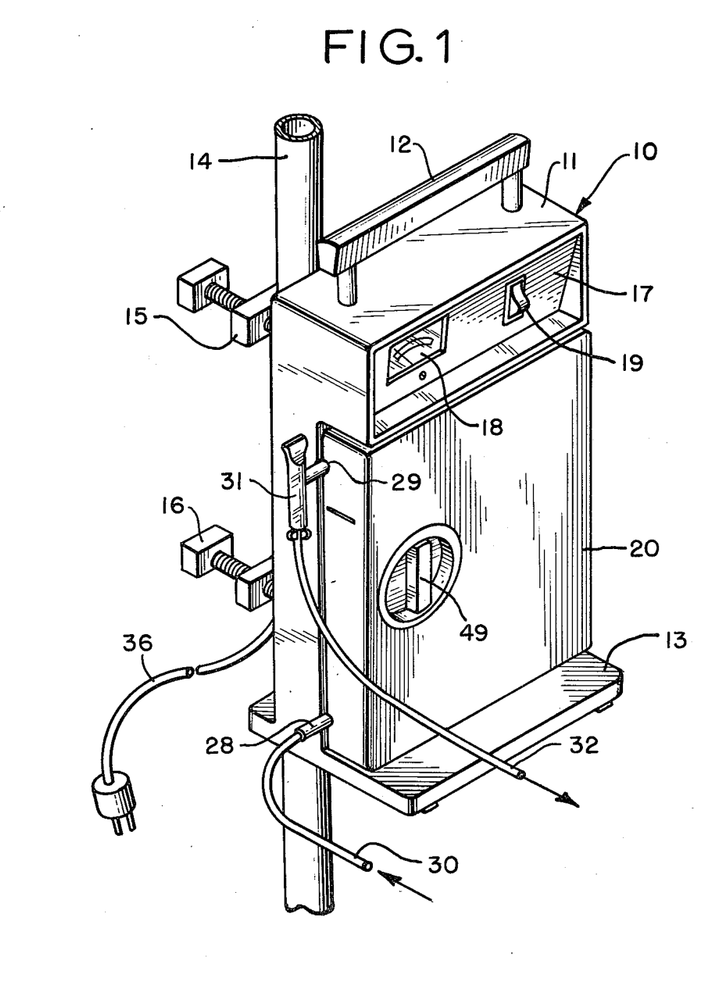
FIG. 1 is a perspective view of a blood warming apparatus constructed in accordance with the invention mounted on a support pole and having a disposable blood warming flow system installed therein.
Figure 2:
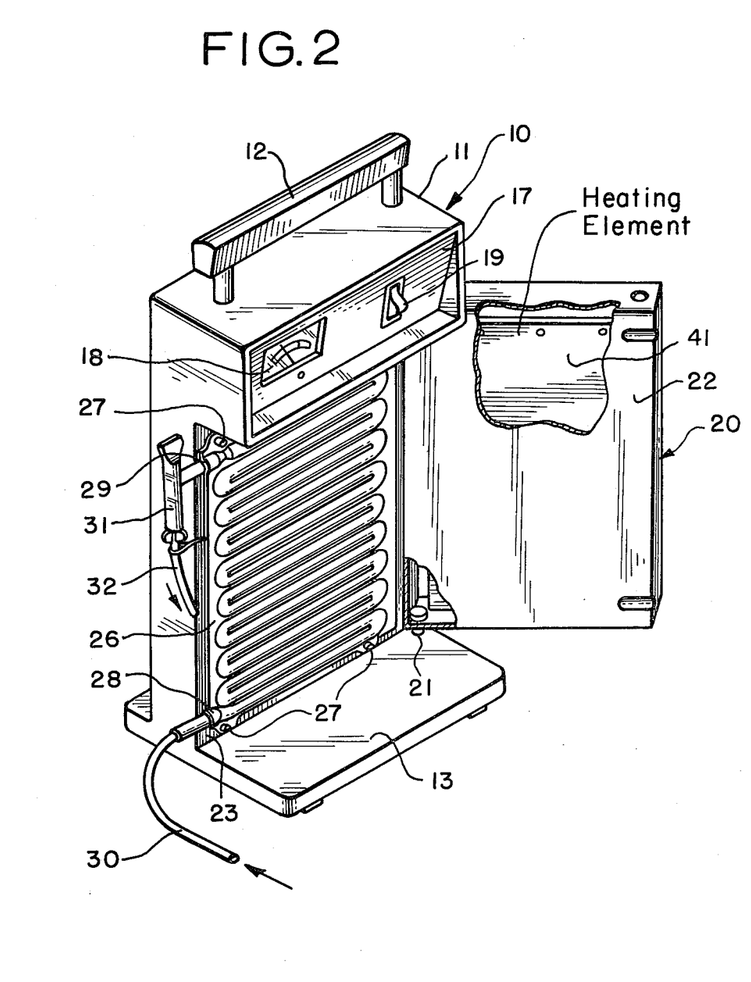
FIG. 2 is a perspective view of the blood warming apparatus set-up on a supporting surface with its heating chamber access door opened and partially broken away to show the internal placement of the blood warming bag of an associated flow system and the location of the heating element within the heating chamber door.
Figures 3, 4, 5, 6:
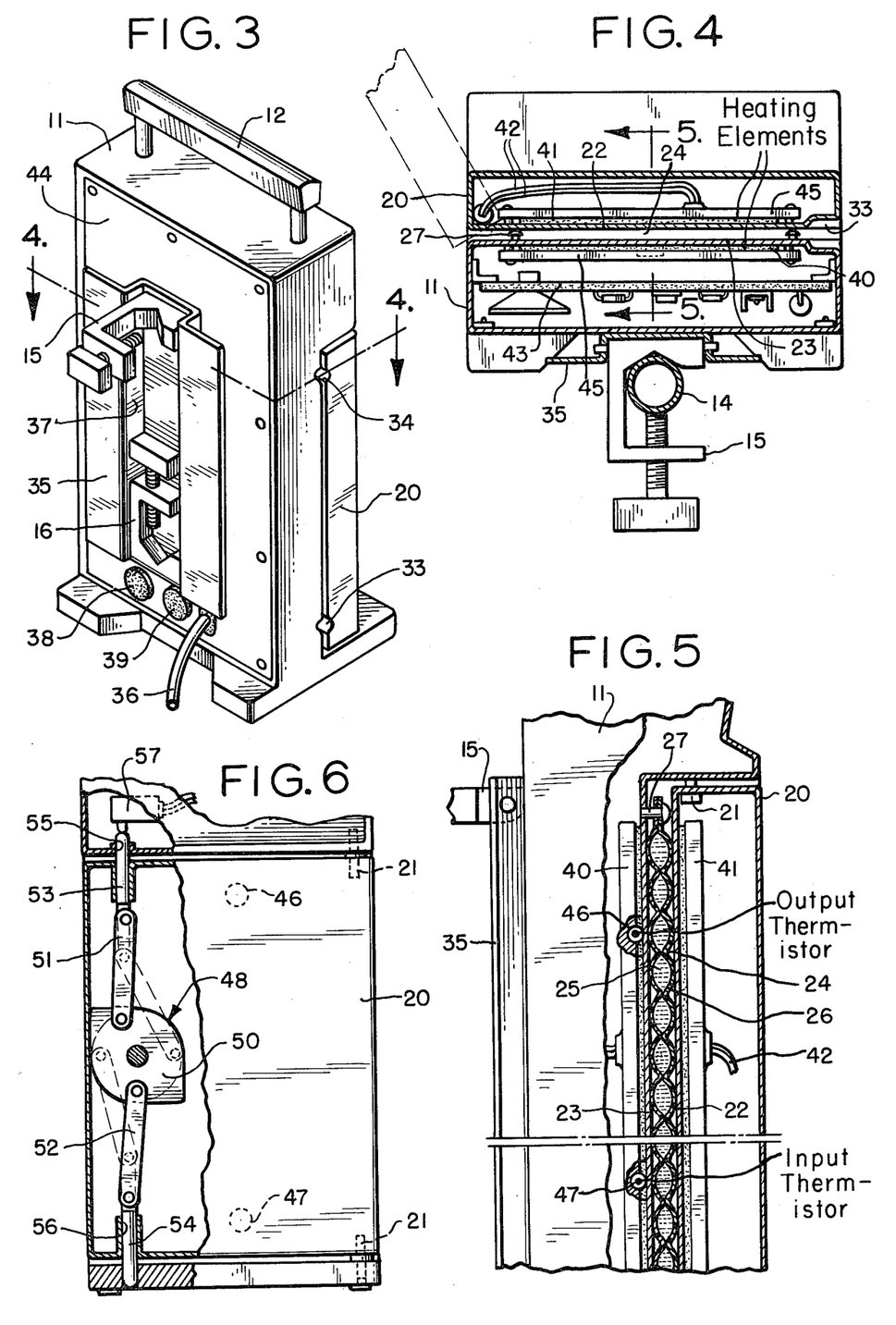
FIG. 3 is a rear perspective view of the blood warming apparatus showing the retractable support clamps and operational test buttons incorporated therein.
FIG. 4 is a cross-sectional view taken along line 4—4 of FIG. 3 showing the interior construction of the apparatus and the utilization of the support clamps for mounting the apparatus to a supporting pole.
FIG. 5 is a cross-sectional view taken along line 5—5 of FIG. 4 showing the placement and construction of the heating elements of the heater apparatus and the placement of the input and output blood temperature sensing elements provided therein.
FIG. 6 is a fragmentary front elevational view of the blood warmer apparatus partially broken away to show the construction and operation of the heating chamber access door latch assembly.

Referring to the Figures, and particularly to FIGS. 1-3, a blood warmer apparatus 10 constructed in accordance with the invention is seen to comprise a generally rectangular housing 11 having a handle portion 12 at its top end and a base portion 13 at its bottom end. In use, the blood warmer apparatus can either be set on a flat supporting surface, as in FIG. 2, in which case the wide base portion 13 provides a high degree of stability, or can be mounted on a vertical support or IV pole 14, as in FIG. 1, wherein a pair of clamps 15 and 16 provided on the rear surface of the apparatus provide the necessary stability.

The blood warmer apparatus is also seen to include in the upper portion of its housing a control panel 17, which may be slightly recessed for protection while the apparatus is in transit and storage. The control panel includes temperature indicating means in the form of a meter 18 which is preferably calibrated to provide a direct readout of blood output temperature, and an ON-OFF power switch 19 which allows the operator to initiate and terminate operation of the blood warmer apparatus.

The blood warmer apparatus 10 includes under panel 17 a heater compartment access door 20 which is pivotably mounted on pins 21 (FIG. 2) to housing 11 at one end so as to open as shown in FIG. 2, providing access to a heating chamber 24 (FIG. 4) formed within the blood warmer apparatus between the inside wall or plate 22 of the door 20 and the underlying wall or plate 23 of housing 11.

Blood warmer apparatus 10 is intended for use in conjunction with a sterile disposable fluid flow system through which whole blood to be warmed is caused to flow, either by means of gravity, pressure or pump feed, to a patient or other utilization means. One such flow system is marketed by Fenwal Laboratories, a division of Travenol Laboratories, Inc., of Deerfield, Illinois, U.S.A., as model No. 4C2416, and is intended for use with a blood administration set for infusing blood from a storage container directly to a patient. The flow system includes a flat generally rectangular warming bag 26 (FIG. 2) which is suspended within chamber 24 by means of a plurality of support pins 27. The warming bag 26 is internally baffled to define a tortuous flow path 25 (FIG. 5) for the blood as it flows from an inlet port 28 at the lower end of the bag to an outlet port 29 at the upper end of the bag. Inlet port 28 is connected by a length of tubing 30 to a container of refrigerated blood (not shown), and outlet port 29 is connected through a chamber 31 and a length of tubing 32 to a needle adapter (not shown), to which a needle is attached for venipuncture. When access door 20 is closed as shown in FIG. 1, the blood warming bag 26 is sandwiched between plate 22 of door 20 and plate 23 of housing 11. When the door 20 is closed connection is established to inlet and outlet ports 28 and 29 through recesses 33 and 34, respectively, provided along the edges of the door and housing. These recesses allow the door to be closed snugly over the warming bag.

Referring to FIG. 3, housing 11 is seen to include on its rear surface a wing-shaped plate 35 which forms a convenient reel around which the power cord 36 of the apparatus can be wound during storage. Bracket 35 also defines an open channel 37 on the rear surface into which clamps 15 and 16 pivot when not in use. Also contained on the rear surface are a pair of push button switches 38 and 39, which when depressed provide first and second tests of the safety monitoring circuits of the blood warmer apparatus.

Referring to FIG. 4, to warm the blood flowing through warming bag 26 the blood warming apparatus includes a first heating element 40 within housing 11 in substantially contiguous contact with the inside surface of plate 23. A second heating element 41 is positioned within door 20 immediately behind and adjacent to the inside plate 22 of the door. The two heating elements are held in position by relatively thick and inflexible plates 45 of insulating material. Electrical power is supplied to this heating element by means of electrical conductors 42 which extend into the interior of housing 11 through the upper pivot hinge 21 (FIG. 6) of door 20. Electrical components and circuitry including a printed wiring board 43 necessary for operation of the blood warmer apparatus 10 are contained within housing 11 behind heating element 40. These items are readily accessible for adjustment and repair by removing the rear plate 44 of housing 11.

Referring to FIG. 5, when access door 20 is closed blood warming bag 26 is sandwiched between plates 22 and 23 so that blood flowing through the interior passageways 25 of the warming bag comes into thermal communication with heating elements 40 and 41. The temperature of the blood flowing through the blood warming bag 26 is sensed by temperature sensing means in the form of a pair of thermistors 46 and 47 located on the center line of recess 24 near the top and bottom of the recess, as shown in FIGS. 5 and 6. Thermistor 47 measures the temperature of the blood flowing through the warming bag near inlet port 28, and thermistor 46 measures the temperature of the blood in bag 26 near outlet port 29. Within the blood warming apparatus thermistors 46 and 47 provide signals indicative of the temperature of the blood discharged from the apparatus as well as the differential temperature which exists between the blood entering the apparatus and the blood being discharged. This information is utilized by control circuitry within the apparatus to control the operation of heating elements 40 and 41, and consequently the temperature to which the blood is heated.

To lock door 20 in a closed position a latch assembly 48 is provided. This assembly includes a user-actuable handle 49 on the outside surface of the door which drives a bell-crank 50 located within the door. The bell-crank is connected by linkages 51 and 52 to locking pins 53 and 54 located on the top and bottom edges of the door. When handle 49 is turned from the extreme counterclockwise position shown to an extreme clockwise position locking pins 53 and 54 are retracted from engagement with aligned recesses 55 and 56 in housing 11 and door 20 is free to open.

When door 20 is locked in its closed position locking pin 53 engages the actuator pin of a switch 57 within housing 11. This switch in conjunction with associated circuitry functions to provide an alarm should the user attempt to unlatch the door while the blood warming apparatus is in operation. To this end switch 57 is arranged so as to be actuated only when locking pin 53 is fully extended so that the alarm will be sounded as the user first attempts to turn handle 49 and before the locking pins have become disengaged from their recesses in housing 11.

Figure 7:
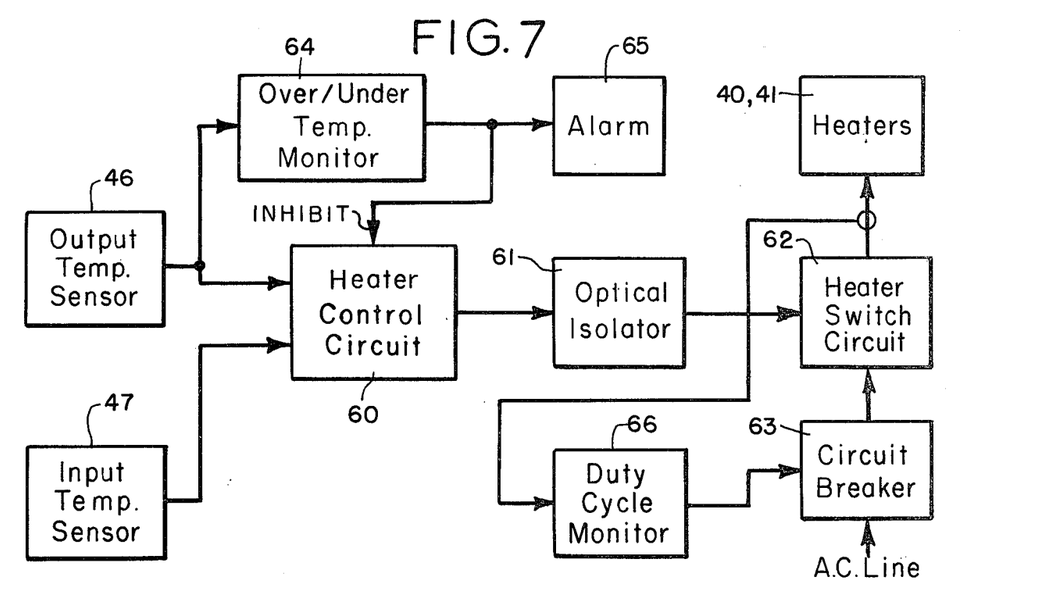
FIG. 7 is a simplified functional block diagram of the blood warmer apparatus showing the principal functional elements thereof.

Referring to FIG. 7, the temperature of the blood discharged from the blood warming apparatus 10 is controlled by means of a heater duty cycle control circuit 60 which causes the heating elements 40 and 41 to be periodically energized with a duty cycle dependent on the temperatures sensed by thermistors 46 and 47. The output of this circuit, which comprises a heater on-off control signal, is applied through an optical isolator 61 to a heater switch circuit 62, which controls application of current to heater elements 40 and 41. Current for powering heaters 40 and 41 is supplied to heater switch circuit 62 from the AC line through a circuit breaker 63 which also functions as a user-actuable power switch and a means of automatically disconnecting power to the unit in the event of a malfunction. Optical isolator 61, which comprises a conventional commercially available component, functions to electrically isolate duty cycle control circuit 60 from the switched AC line and the other control circuits of the blood warming apparatus to minimize leakage between the AC line and the patient under treatment.

In accordance with the invention, the heater duty cycle control circuit 60 varies the duty cycle of heaters 40 and 41 both as a function of the output temperature sensed by sensor 46, and as a function of the differential between the input and output temperature of the blood as sensed by sensors 46 and 47. As the output temperature of the blood increases beyond the desired level control circuit 60 functions to reduce the duty cycle of heaters 40 and 41, thus lowering the output temperature to the desired level. Conversely, as the output temperature of the blood decreases below the desired level control circuit 60 functions to increase the duty cycle of the heaters, thus increasing the blood temperature to the desired level. At the same time, should the differential in sensed temperatures increase, signifying an increase in blood flow rate, the duty cycle of heaters 40 and 41 is automatically increased to compensate for the increased flow rate and avoid the output temperature of the blood falling below the desired level. Conversely, as the difference between the sensed input and output temperatures decreases, signifying a reduced flow rate, the duty cycle of the heaters is automatically reduced to avoid heating the blood beyond the desired level.

Protection is provided against malfunction of the control circuit by means of a first alarm circuit comprising an over-under temperature monitor circuit 64 which provides an output in the event that the blood output temperature, as sensed by sensor 46, rises above a predetermined maximum temperature of falls below a predetermined minimum temperature. In practice, the maximum temperature limit is set just slighly above the nominal body temperature to 37° C. to avoid any possibility of damage to the blood being processed, and the minimum temperature limit is set at approximately 0° C. so as to sense a failure of the output temperature sensor 46.

In the event of an output from temperature monitor 64 indicating either an over or under temperature condition, an alarm 65 is actuated to indicate to the user that a malfunction has occurred. Simultaneously, the application of control signals from control circuit 60 to the heater switch circuit 62 is interrupted to prevent further heating of the blood by heating elements 40 and 41.

The blood warming apparatus 10 incorporates a second monitoring circuit 66 which monitors current supplied to heating elements 40 and 41. During normal operation this current is periodically switched on and off at a rate determined by control circuit 60. Should a malfunction occur which results in a continuous current being applied to heaters 40 and 41, duty cycle monitor 66 generates an output signal which is applied to an appropriate terminating device in circuit breaker 63 to interrupt power to the blood warming apparatus. In practice, duty cycle monitor 66 is constructed to terminate operation whenever power to the heating elements is not interrupted in a 3 second interval.

A further feature of the control arrangement shown in FIG. 7 is that power to the heating element is switched on only during those portions of the applied AC line current when that current is passing through its zero axis. This is done to minimize transients which would otherwise be generated by switching during periods of current flow through the heating elements, and to minimize the attendant radio frequency interference produced as a result of such transients.

Figure 8:
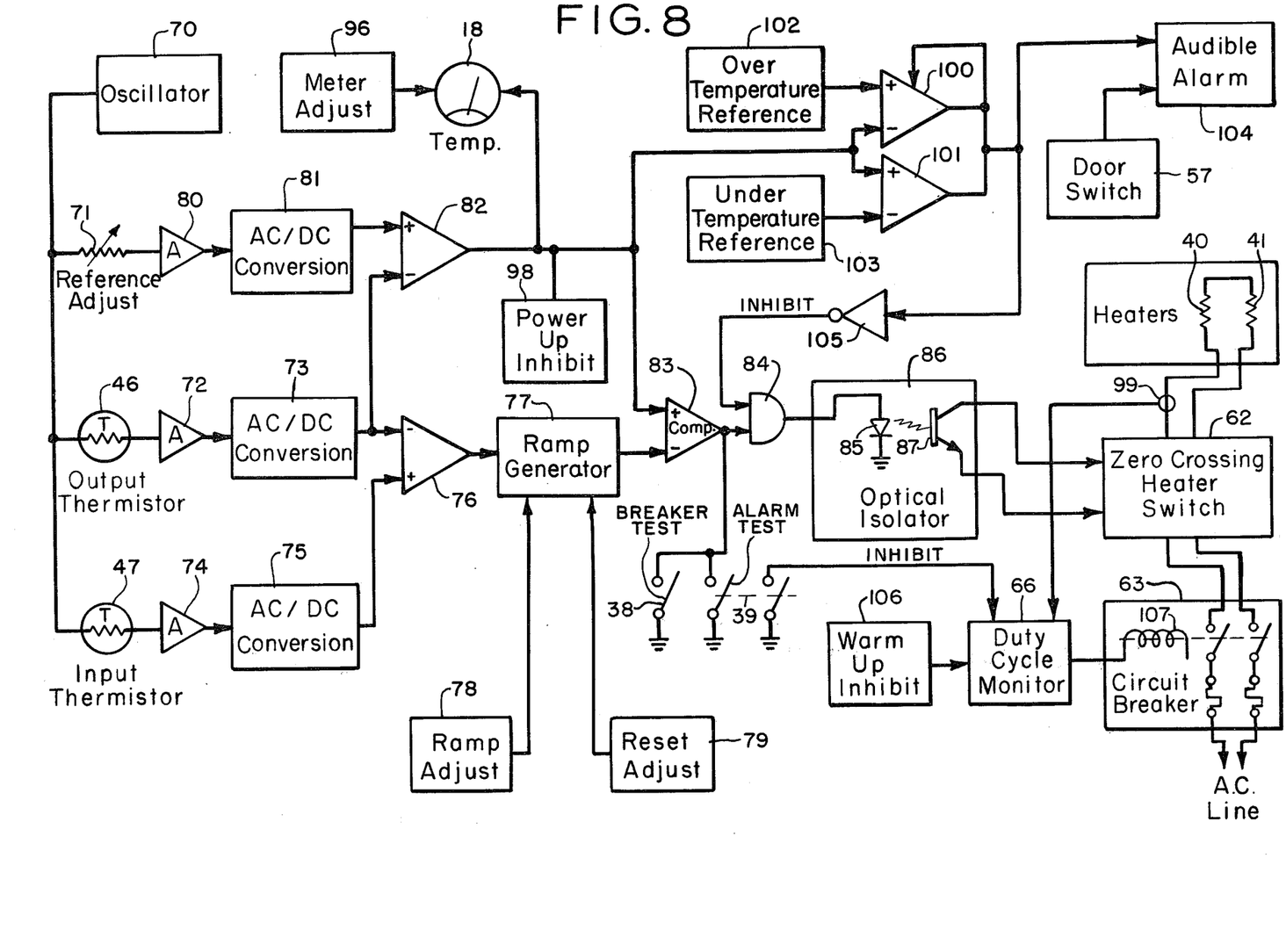
FIG. 8 is a functional block diagram of the blood warmer apparatus showing the functional elements thereof.

In further accord with the invention, the heater control signal applied to heater switch circuit 62 is generated within control circuit 60 by means of a novel slope-intercept system. Referring to FIG. 8, control circuit 60 includes an oscillator 70 which generates a square wave signal at approximately 20 kilohertz. This signal is simultaneously applied to thermistors 46 and 47 and to a reference adjust potentiometer 71. Thermistor 46 is connected in a voltage divider circuit (not shown) to provide at the input of an amplifier 72 a square wave signal amplitude-dependent on the output temperature of the blood being processed. This signal is amplified in amplifier 72 and applied to an AC-DC conversion stage 73 wherein it is converted to an analog signal indicative of the output temperature of the blood. Similarly, thermistor 47 develops a variable-amplitude square wave signal which is amplified in an amplifier 72 and converted to an analog input temperature-indicative signal in an AC-DC conversion stage 75.

The analog signals from conversion stages 73 and 75 are applied to the inverting and non-inverting inputs of a first differential amplifier 76 which produces an output signal indicative of the difference between the two applied signals. Their output signal is applied to a ramp generator 77 which generates repetitive ramp voltage functions each having a slope which varies inversely with the amplitude of the applied signal. Ramp generator 77, which may be any of a number of known circuits for this purpose, includes a circuit provision 78 for setting the initial slope of the ramp in the absence of an applied differential signal, and a circuit provision 79 for establishing the reset voltage level at which point the ramp generator recycles. In practice, the slope of the ramp and the recycle level are such that the ramp function is repeated nominally every 600 milliseconds. This is a relatively long control period relative to the 16.7 millisecond period of the 60 hertz AC line which supplies current to the heating elements and must be switched on and off, and a relatively short period compared to the thermal inertia of the blood warming apparatus so as not to constitute a limiting factor in system performance.

The reference adjust potentiometer 71 provides a square wave signal of adjustable amplitude which once set varies only with variations in the amplitude of the square wave signal produced by oscillator 70. This signal is amplified in an amplifier 80 and applied to an AC-DC conversion stage 81, wherein it is converted to a temperature-dependent oscillator amplitude-dependent analog signal. This analog signal is applied to the non-inverting input of a second differential amplifier 82. The analog signal from conversion stage 73 is applied to the other inverting input of amplifier 82 to develop an output signal therefrom which constitutes an output temperature-indicative signal independent of amplitude variations in oscillator 70.

The output temperature-indicative signal from differential amplifier 82 is applied to the non-inverting input of a voltage comparitor 83, and the variable-slope repetitive ramp function generated by ramp generator 77 is applied to the inverting input of this comparitor. As the instantaneous voltage level of the ramp function increases with time, a point is eventually reached at which the ramp and temperature-indicative functions become equal. At this point an output is produced by comparitor 83 which constitutes the desired heating element control signal.

The heater control signal is applied to one input of an AND gate 84. The output of this gate is applied to a light emitting diode (LED) 85 which preferably comprises an integral element of a conventional optical isolator component 86. In a manner well known to the art, within isolator 86 the light emitted by LED 85 establishes conduction in an optically adjacent semiconductor device 87. The semiconductor device is connected to the zero crossing heater switch 62 wherein when conductive it conditions the switch to a conductive state to energize heating elements 40 and 41. As previously stated, switching of the AC current supplied to the heaters is preferably accomplished only when the AC waveform crosses its zero axis since at this instant current flow through the heating element is at a minimum and minimum radio frequency interference is generated. The circuitry for accomplishing this is well known to the art, and therefore is not described in detail herein.

Figure 9:
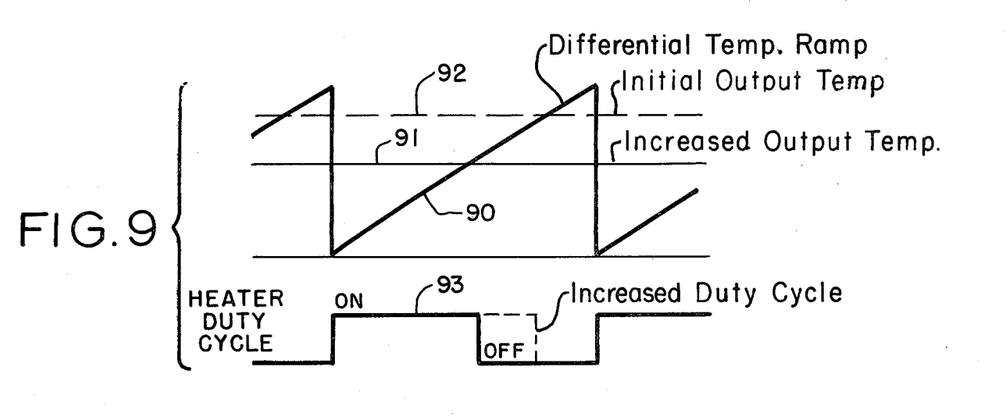
FIG. 9 is a graphical depiction of the operation of the blood warmer apparatus illustrating the effect of variations in blood output temperature on the duty cycle of the heating elements contained therein.
Figure 10:
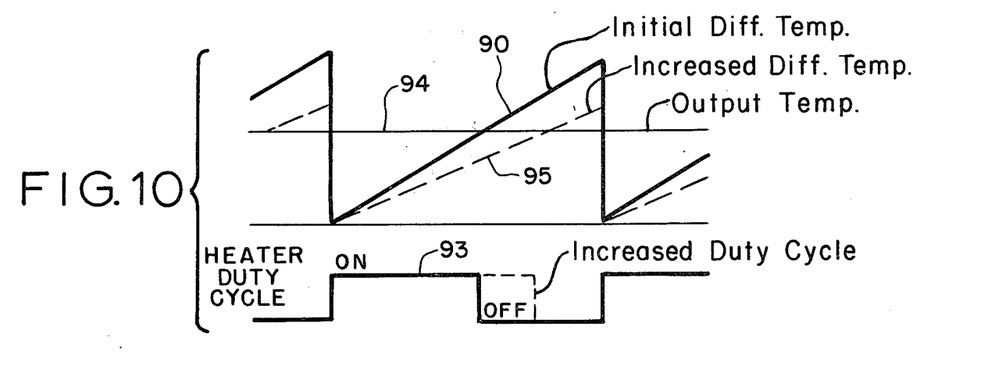
FIG. 10 is a graphical depiction of the operation of the blood warmer apparatus illustrating the effect of variations in flow rate on the duty cycle of the heating elements contained therein.

Since an output is developed by comparitor 83 only when the voltage levels applied to its inputs are equal or of a positive relationship, the duty cycle of the output signal developed by comparitor 83 is dependent on both the absolute temperature of the discharged blood, as signified by the analog signal applied from differential amplifier 82, and the difference between the input and output blood temperatures, is signified by the slope of the repetitive ramp voltage function applied from ramp generator 77. This is illustrated in FIGS. 9 and 10. In FIG. 9 it is seen that the waveform 90 representing the ramp function generated by ramp generator 77 for a constant temperature differential intersects the higher voltage level 92 corresponding to an initial output temperature later than it intersects a voltage level 91 corresponding to an increased output temperature. As a result the heater-on duty cycle, as depicted by waveform 93, is increased with increased voltage levels accompanying decreases in blood output temperature.

The effect of variations in temperature differential is illustrated in FIG. 10. For an initial differential temperature the waveform 90 of the ramp function intersects the voltage level 94 corresponding to the blood output temperature and terminates the heating cycle earlier than when the slope has decreased because of an increased temperature differential, as shown by waveform 95. The result is the duty cycle of the heater, as depicted by waveform 93, increases to enable the blood warming apparatus 10 to accommodate the increased flow rate which brought about the increased temperature differential.

In practice, both temperature differential and blood output temperature vary with time, and the resulting duty cycle is a composite of both of these variables. Of particular advantage is the fast response time this circuit arrangement provides as compared to prior art thermostatically-controlled blood warming apparatus wherein the heater elements were energized only on demand.

To provide an indication to the user of the temperature of the blood discharged from the blood warming apparatus the analog output signal developed by differential amplifier 82 is applied to meter 18, which has previously been described as having a temperature-indicating scale. To enable meter 18 to provide a direct reading of temperature, the meter circuit preferably includes a meter-adjust circuit provision 96 which partly offsets the voltage applied to the meter to calibrate the meter in a manner well known to the art.

In accordance with another aspect of the invention, the temperature of the discharged blood is continuously monitored by means of a high and low limit comparison circuit formed by differential amplifiers 100 and 101. The temperature indicative output signal from differential amplifier 82 is applied to the inverting input of differential amplifier 100, and a reference signal developed in an over-temperature reference source 102 is applied to the non-inverting input of this device. The output of amplifier 100 includes a feedback network so that when the measured temperature exceeds the over-temperature reference, amplifier 100 is locked in an on state until subsequently reset by removal of power from the apparatus.

The output of differential amplifier 82 is also coupled to the non-inverting input of differential amplifier 101, the inverting input of which is connected to an under-temperature reference voltage source 103. The output of this amplifier is coupled to the output of amplifier 100, so that if the voltage level developed by differential amplifier 82 falls below that from reference 103 an output is developed from amplifier 101 which locks amplifier 100 in an on state as if that amplifier had detected the over-temperature condition. Thus, upon occurrence of either an over-temperature or under-temperature condition, an output is developed which remains until power is removed from the apparatus.

The alarm signal from amplifiers 100 and 101 is applied to an alarm 104 which sounds an audible alarm to alert the user that the blood output temperature is out of limits. Alarm 104 is also actuated by door switch 57 should the user attempt to open the door during operation of the blood warming apparatus.

The alarm signal developed by differential amplifiers 100 and 101 is also applied through an inverter 105 to the remaining input of AND gate 84 to inhibit that gate upon occurrence of an alarm condition. Since inhibiting this gate has the effect of preventing actuation of the heater control signal to optical isolator 86 and heater switch 62, the application of power to heating element 40 and 41 is terminated. A power-up inhibit circuit 98 provides an alarm inhibiting voltage at the output of amplifier 82 for a short period of time, typically in the order of a few seconds, upon initial operation of the blood warming apparatus to prevent actuation of the temperature alarm.

As previously stated, the duty cycle monitor 66 monitors the AC current applied to heater elements 40 and 41 to ascertain the correct functioning of the heater control circuit 60, optical isolator 86, and zero-crossing heater switch 62. This is accomplished by means of a current probe 99 to avoid a direct electrical connection between the monitor circuit and the AC line to preclude leakage from the line to the patient. Since the monitor produces an output only in the event that power to the heaters is not interrupted over a three second interval, and the nominal duty period of the heaters is 600 milliseconds, the monitor normally will only actuate in the event of a malfunction. However, during initial operation of the blood warming apparatus it is possible, particularly when the apparatus is cold, that the duty cycle control circuit will as a result of sensing a low output temperature call for continuous operation of the heater elements. To prevent the duty cycle monitor 66 from interpreting this normal warm-up mode of operation as a fault, the blood warming apparatus preferably includes a warm-up inhibit circuit 106 which inhibits the operation of the duty cycle monitor 66 for a predetermined time period following initial power up of the apparatus. Typically, this time period is set at approximately two minutes, which has been found adequate to bring plates 22 and 23 up to operating temperature in even abnormally cold conditions.

After the initial warm-up period has passed, and duty cycle monitor 66 detects a fault, a signal is applied to a solenoid 107 associated with circuit breaker 63 to trip the circuit breaker to an open condition, thus removing all power from the blood warming apparatus. It will be observed that, in accordance with another aspect of the invention, the circuit breaker 63 of the apparatus can be tripped in three ways; (1) manually by the user, (2) electrically by solenoid 107, and (3) by a short circuit or ground fault within the apparatus or heater elements causing the breaker to trip as a result of the ensuing overload.

The heater elements 40 and 41 which preferably comprise 350 watt pad-type units, are preferably connected in series so that should one element become open the other element will be rendered inoperative.

To provide a positive test of the operability of the various monitoring circuits, the blood warming apparatus preferably includes a breaker test function initiated by the push button switch 38 on the rear panel of housing 11. After a two minute delay after power is applied, actuation of this switch causes a continuous signal to be applied to optical isolator 86, and hence to heater switch 62. Since this results in heater elements 40 and 41 being continuously powered, if duty cycle monitor 66 is operative a control signal will be developed after approximately three seconds, which will trip circuit breaker 63 and cause power to be removed from the blood warming apparatus.

To provide a positive test of its alarm circuitry, the blood warming apparatus includes an alarm test function which is initiated by the push button switch 39 located on the rear panel of housing 11. This switch, when actuated, causes a continuous current to be applied to the heater elements, while at the same time inhibiting the duty cycle monitor 66. Now, circuit breaker 63 is not tripped and the heaters remain energized to raise the temperature of the heating elements until the temperature of the elements becomes greater than the upper limit temperature set by reference 102. At this point differential amplifier 100 is locked to an on state, generating an output signal which actuates alarm 104 and inhibits AND gate 84 to remove power from the heating elements. Thus, the blood warming apparatus of the invention includes provisions for completely and conveniently testing its internal monitoring circuitry to assure that a malfunction of the heater control circuitry will not result in delivery of blood outside of a desired temperature range.

Figure 11:
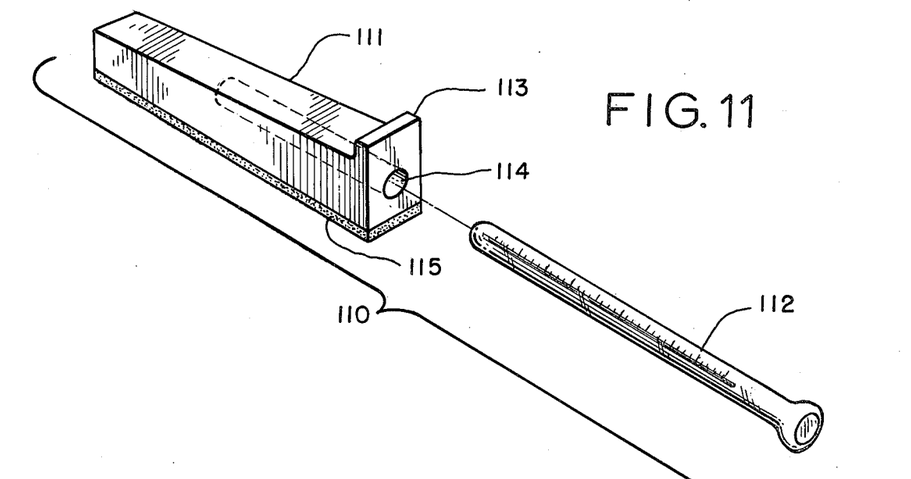
FIG. 11 is an exploded perspective view of a temperature measurement assembly utilized to verify and adjust the operation of the blood warmer apparatus.
Figure 12:
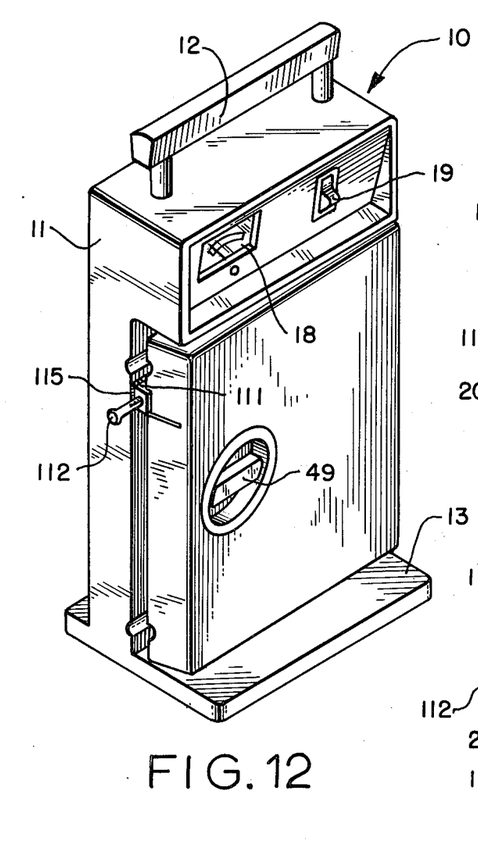
FIG. 12 is a front perspective view of the blood warmer apparatus showing the placement of the temperature measurement assembly therein to verify and adjust for proper operation.

To confirm the accuracy of the temperature indicated by meter 18, and to provide an independent check of the operation of the heating elements, the blood warming apparatus may include a temperature measurement assembly 110 adapted to be inserted in the heating chamber 24 of the apparatus. Referring to FIG. 11, this assembly includes a thermometer block 111 and a thermometer 112. The thermometer block 111 is preferably rectangular in cross section, and wedge-shaped to provide an interface with plates 22 and 23 when inserted into heating compartment 24 with the door partially open, as shown in FIG. 12. In practice, this is done with the blood warming apparatus setting on its rear surface, so that the thermometer block 111 and thermometer 112 will more readily remain in position. A flange portion 113 at the outside end of the thermometer block facilitates positioning the block within the heating chamber, and an aperture 114 is provided at this end for receiving thermometer 112, which may comprise a standard oral thermometer.

Figure 13A:
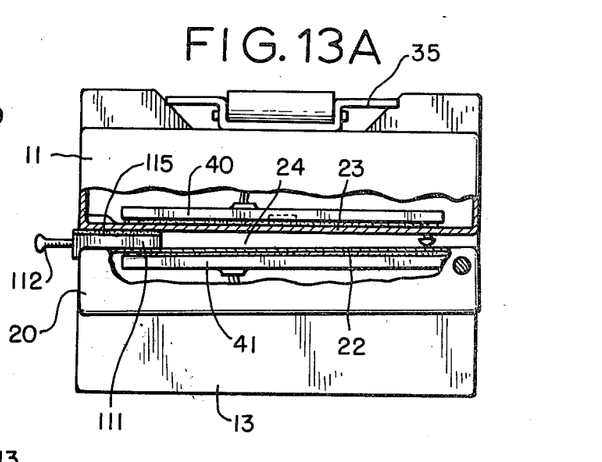
FIGS. 13A and 13B are cross-sectional views taken along line 13—13 of FIG. 12 showing the positioning of the temperature measuring assembly of FIG. 11 to measure and verify the operation of the housing and door mounted heating elements of the blood warmer apparatus, respectively.
Figure 13B:
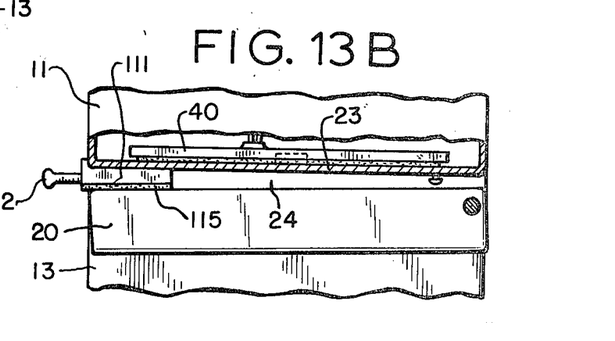

To enable the thermometer block to selectively measure the temperature of either the door heating plate 22 or the base heating plate 23, the thermometer block is preferably provided with a layer of heat-insulating material 115 along one face thereof. As shown in FIG. 13A, when this insulating layer is positioned toward plate 23 thermometer 112 reads the temperature of the heating plate 22 associated with door 20, whereas when the insulating layer is positioned toward plate 22, as shown in FIG. 13B, thermometer 112 reads the temperature of plate 23 associated with housing 11.

The blood warming apparatus of the invention provides a convenient to use easily transportable device useful for warming blood and other parental fluids prior to infusion into a patient. The apparatus is completely automatic in operation, requiring only that the user position a blood heating bag associated with an infusion set into the apparatus, perform the precautionary test functions to ascertain the operability of the monitoring features of the apparatus, and then proceed with the infusion. Since the apparatus is a dry heat system intended for use with a blood warming bag and blood infusion set, no water bath or time-consuming preparation is required. Typically, blood infused through the apparatus is maintained within a temperature range of 30° C. to 37° C. with flow rates varying from 0 to 150 ml per minute.

It will be appreciated that while the invention is particularly well suited for heating blood, it also finds utility in other applications where a highly accurate fluid output temperature must be maintained over a wide range of flow rates, and that the nominal operating temperatures and time periods given by way of example in the blood warming application will change for such other applications.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. Fluid warming apparatus for heating a refrigerated fluid such as blood to a predetermined nominal temperature prior to infusion at flow rates variable over a substantially predetermined range, said apparatus comprising, in combination:

housing means defining a heating chamber for the fluid within the apparatus, the fluid having an input temperature and an output temperature within said chamber;

at least one electric heater element operable from an applied electric current in thermal communication with the fluid in said heating chamber for heating the fluid as it passes through the apparatus;

control circuit means responsive to said input and output temperatures of the fluid for generating a heater control signal dependent on both said output temperature and flow rate of the fluid;

said control circuit means including first temperature sensing means for sensing the input temperature of the fluid and developing a first output signal indicative thereof, second temperature sensing means for sensing the output temperature of the fluid and developing a second output signal indicative thereof, a differential amplifier for developing from said first and second output signals a differential signal indicative of the differential between said input and output temperatures; said heater control signal being variable as a function of both said output temperature of the fluid and said differential signal; and switch circuit means electrically connected between said heating element and a source of electrical current, and responsive to said heater control signal for controlling the application of current to said heating element, for maintaining the fluid at the predetermined nominal temperature notwithstanding variations in the flow rate thereof.

2. Fluid warming apparatus as defined in claim 1 wherein said control circuit means establish a recurring on-off duty cycle for said heater element dependent on the output temperature and temperature differential of said fluid in said apparatus.

3. Fluid warming apparatus as defined in claim 2 wherein said control circuit means further include a ramp generator for generating a recurrent voltage ramp function having a slope which varies inversely with said differential signal, and voltage comparison means for comparing said ramp function with said second temperature-indicative output signal to generate a heater control signal providing an on-off duty cycle dependent on said output temperature and said temperature differential.

4. Fluid warming apparatus as defined in claim 2 wherein said apparatus includes duty cycle monitor circuit means for initiating an alarm condition upon application of current to said heating element for a predetermined period of time greater than the nominal period of said duty cycle.

5. Fluid warming apparatus as defined in claim 4 wherein said duty cycle monitor circuit means include current probe means for monitoring current flow to said heating element without establishing a direct electrical connection thereto.

6. Fluid warming apparatus as defined in claim 4 including circuit means for inhibiting the operation of said duty cycle monitor for a predetermined period of time following initial power-up of the apparatus.

7. Fluid warming apparatus as defined in claim 1 wherein said heating element is operable from an applied alternating current, and said switch circuit means switch current to said heating element only during zero-crossing portions of said alternating current cycle.

8. Fluid warming apparatus as defined in claim 1 wherein said heating element is operable from an applied alternating current, and the output of said control circuit means is optically coupled to said switch circuit means to maintain electrical isolation therebetween.

9. Fluid warming apparatus as defined in claim 1 wherein the fluid is conveyed within a sterile disposable flow system having a warming bag dimensioned to fit within said heating chamber, said housing means including an access door providing access to said heating chamber, said door having latching means thereon for locking said door in a closed position with said warming bag within said chamber, and wherein alarm means are provided for providing an alarm upon actuation of said latching means away from a locked condition during operation of the apparatus.

10. Fluid warming apparatus as defined in claim 1 wherein said fluid is conveyed within a sterile disposable flow system having a generally flat warming bag dimensioned to fit within said heating chamber, and said apparatus includes a pair of said heating elements arranged on opposite sides of said warming bag and electrically connected in series-circuit relationship.

11. Fluid warming apparatus as defined in claim 1 including temperature monitoring circuit means responsive to the output temperature of the fluid for providing an alarm when said output temperature rises above or falls below a predetermined range.

12. Fluid warming apparatus for heating a refrigerated fluid such as blood to a predetermined nominal temperature as it flows through a disposable flow system including a warming bag at flow rates variable over a substantial predetermined range, said apparatus comprising, in combination:

housing means defining a heating chamber within the apparatus for receiving the warming bag;

at least one electric heater element operable from an applied electric current for heating the fluid as it passes through the warming bag;

control circuit means responsive to the input and output temperature of the fluid in the warming bag for generating a heater control signal providing an on-off duty cycle dependent on both the output temperature of the fluid and the differential between the input and output temperatures of the fluid; said heater control signal being variable as a function of both said output temperature of the fluid and said differential signal; and switch circuit means electrically connected between said heating elements and a source of electrical current and responsive to said heater control signal for controlling the application of current to the heating element in accordance with said control signal to maintain the output temperature of the fluid substantially constant at said predetermined nominal temperature notwithstanding variations in the flow rate thereof.

13. Fluid warming apparatus as defined in claim 12 wherein said control circuit means include first temperature sensing means for sensing the input temperature of the fluid and developing a first output signal indicative thereof, second temperature sensing means for sensing the output temperature of the fluid and developing a second output signal indicative thereof, and differential amplifier means for developing from said first and second output signals a differential signal indicative of the differential between said input and output temperatures.

14. Fluid warming apparatus as defined in claim 13 wherein said control circuit means further include a ramp generator for generating a recurrent voltage ramp function having a slope which varies inversely with said differential signal, and voltage comparison means for comparing said ramp function with said second temperature-indicative output signal to generate a heater control signal providing an on-off duty cycle dependent on said output temperature and said temperature differential.

15. Fluid warming apparatus as defined in claim 12 wherein said apparatus includes duty cycle monitor circuit means for initiating an alarm condition upon application of current to said heating element for a predetermined period of time greater than the nominal period of said duty cycle.

16. Fluid warming apparatus as defined in claim 15 wherein said duty cycle monitor circuit include current probe means for monitoring current flow to said heating element without establishing a direct electrical connection thereto.

17. Fluid warming apparatus as defined in claim 15 including circuit means for inhibiting the operation of said duty cycle monitor for a predetermined period of time following initial power-up of the apparatus.

18. Fluid warming apparatus as defined in claim 12 wherein said heating element is operable from an applied alternating current, and said switch circuit means switch current to said heating element only during zero-crossing portions of said alternating current cycle.

19. Fluid warming apparatus as defined in claim 12 wherein said heating element is operable from an applied alternating current, and the output of said control circuit means is optically coupled to said switch circuit means to maintain electrical isolation therebetween.

20. Fluid warming apparatus as defined in claim 12 wherein said housing means include an access door providing access to said heating chamber, said door having latching means for locking said door in a closed position with said warming bag within said chamber, and wherein alarm means are provided for sounding an alarm upon actuation of said latching means away from a locked condition during operation of the apparatus.

21. Fluid warming apparatus as defined in claim 12 wherein said warming bag is flat and dimensioned to fit within said heating chamber, and wherein the apparatus comprises a pair of said heating elements on either side of said warming bag and electrically connected in series-circuit arrangement.

22. Fluid warming apparatus as defined in claim 12 including temperature monitoring circuit means responsive to the output temperature of the fluid for providing an alarm when said output temperature rises above or falls below a predetermined range.

23. Fluid warming apparatus for heating a refrigerated fluid such as blood to a predetermined nominal temperature as it flows through a disposable flow system including a warming bag at flow rates variable over a substantial predetermined range, said apparatus comprising in combination:

housing means defining a heating chamber within the apparatus for receiving the blood warming bag;

at least one electrical heating element operable from an applied electrical current and disposed in thermal communication with the warming bag when the bag is seated within said heating chamber for heating the fluid as it passes through the warming bag;

first temperature sensing means for sensing the input temperature of the fluid in said warming bag and developing a first output signal indicative thereof;

second temperature sensing means for sensing the output temperature of the fluid within said bag and developing a second output signal indicative thereof;

differential amplifier means for developing from said first and second output signals a differential signal indicative of the difference between said input and output temperatures;

a ramp generator for generating a voltage ramp function having a slope which varies inversely with said differential signal;

voltage comparison means for comparing said voltage ramp function with said second temperature-indicative output signal to generate a heater control signal providing a duty cycle which varies as a function of both the output temperature of the fluid and the differential between the input and output temperature of the fluid; and switch circuit means electrically connected between said heating element and a source of current and responsive to said heater control signal for controlling the application of current to said heating element in accordance with said control signal to maintain the output temperature of the fluid substantially constant at the predetermined nominal temperature notwithstanding variations in the flow rate thereof.

24. Fluid warming apparatus as defined in claim 23 wherein said apparatus includes a duty cycle monitor circuit means for initiating an alarm condition upon application of current to said heating element for a predetermined period of time greater than the nominal period of said duty cycle.

25. Fluid warming apparatus as defined in claim 24 wherein said duty cycle monitor circuit means include current probe means for monitoring current flow to said heating element without establishing a direct electrical connection thereto.

26. Fluid warming apparatus as defined in claim 24 including circuit means for inhibiting the operation of said duty cycle monitor for a predetermined period of time following initial power-up of the apparatus.

* * * * *

UNITED STATES PATENT AND TRADEMARK OFFICE
CERTIFICATE OF CORRECTION

PATENT NO. : 4,167,663
DATED : September 11, 1979
INVENTOR(S) : Daniel Granzow, Jr. and Robert Froehlich It is certified that error appears in the above-identified patent and that said Letters Patent are hereby corrected as shown below:

Column 13, line 49, after "circuit", insert --means--.

*Signed and Sealed this*

*Twenty-ninth* Day of *January 1980*

[SEAL]

*Attest:*

SIDNEY A. DIAMOND

*Attesting Officer*  *Commissioner of Patents and Trademarks*